United States Patent
Zhao et al.

(10) Patent No.: US 10,214,480 B2
(45) Date of Patent: Feb. 26, 2019

(54) SYNTHESIS PROCESS FOR CHIRAL CYCLOPROPYL ETHYNYL TERTIARY ALCOHOL COMPOUND

(71) Applicants: Shanghai Desano Pharmaceutical Co., Ltd., Shanghai (CN); Yancheng Desano Pharmaceutical Co., Ltd., Jiangsu (CN); Jiangsu Puxin Pharmaceutical Co., Ltd., Jiangsu (CN)

(72) Inventors: Nan Zhao, Shanghai (CN); Fei Jiang, Shanghai (CN)

(73) Assignees: Shanghai Desano Pharmaceutical Co., Ltd., Shanghai (CN); Yancheng Desano Pharmaceutical Co., Ltd., Jiangsu (CN); Jiangsu Puxin Pharmaceutical Co., Ltd., Jiangsu (CN)

( * ) Notice: Subject to any disclaimer, the term of this patent is extended or adjusted under 35 U.S.C. 154(b) by 0 days.

(21) Appl. No.: 15/551,142

(22) PCT Filed: Oct. 23, 2015

(86) PCT No.: PCT/CN2015/092754
§ 371 (c)(1),
(2) Date: Aug. 15, 2017

(87) PCT Pub. No.: WO2016/127661
PCT Pub. Date: Aug. 18, 2016

(65) Prior Publication Data
US 2018/0029975 A1    Feb. 1, 2018

(30) Foreign Application Priority Data

Feb. 15, 2015  (CN) .................. 2015 1 0083083
Jun. 10, 2015  (CN) .................. 2015 1 0316165

(51) Int. Cl.
| | | |
|---|---|---|
| C07C 213/10 | (2006.01) | |
| C07C 213/00 | (2006.01) | |
| C07C 215/70 | (2006.01) | |
| C07D 265/18 | (2006.01) | |
| C07B 53/00 | (2006.01) | |

(52) U.S. Cl.
CPC ............ *C07C 213/10* (2013.01); *C07B 53/00* (2013.01); *C07C 213/00* (2013.01); *C07C 215/70* (2013.01); *C07D 265/18* (2013.01); *C07B 2200/07* (2013.01); *C07C 2601/02* (2017.05)

(58) Field of Classification Search
None
See application file for complete search history.

(56) References Cited

U.S. PATENT DOCUMENTS

| | | | |
|---|---|---|---|
| 6,015,926 A | 1/2000 | Chen et al. | |
| 7,439,400 B2 * | 10/2008 | Jiang .................... | C07C 213/02 556/422 |
| 8,115,032 B2 | 2/2012 | Chinkov et al. | |
| 8,283,502 B2 | 10/2012 | Chinkov et al. | |
| 8,957,204 B2 | 2/2015 | Brenner et al. | |
| 8,969,550 B2 | 3/2015 | Brenner et al. | |
| 8,999,964 B2 | 4/2015 | Pellicciari | |
| 2011/0172464 A1 | 7/2011 | Chinkov et al. | |
| 2011/0263555 A1 | 10/2011 | Pellicciari | |
| 2012/0029237 A1 | 2/2012 | Chinkov et al. | |
| 2013/0211077 A1 | 8/2013 | Brenner et al. | |
| 2013/0217875 A1 | 8/2013 | Brenner et al. | |

FOREIGN PATENT DOCUMENTS

| | | |
|---|---|---|
| CN | 1255919 A | 6/2000 |
| CN | 1449865 A | 10/2003 |
| CN | 1331601 C | 8/2007 |
| CN | 101125834 A | 2/2008 |
| CN | 101786959 A | 7/2010 |
| CN | 102617366 A | 8/2012 |
| CN | 103249724 A | 8/2013 |

(Continued)

OTHER PUBLICATIONS

CN101786959 machine translation from Google patents obtained Jan. 2017.*
International Search Report dated Jan. 27, 2016 issued in corresponding PCT/CN2015/092754 application (5 pages).
B. Jiang et al., "Alkynylation of Carbonyl Compounds With Terminal Acetylenes Promoted by ZnCl2 and Et3N: Simple, Mild and Efficient Preparation of Propargylic Alcohols", Tetrahedron Letters, vol. 43, No. 46 (2002) pp. 8323-8325.

(Continued)

*Primary Examiner* — Clinton A Brooks
(74) *Attorney, Agent, or Firm* — Millen White Zelano and Branigan, PC; Csaba Henter

(57) ABSTRACT

Provided is a synthesis process for a chiral cyclopropyl ethynyl tertiary alcohol compound, where a chiral amino alcohol or a chiral amino diol is reacted in the presence of an alkaline reagent and a salt to obtain an optically active propynyl alcohol compound. In particular, the process includes (1) reacting cyclopropyl acetylene with a chiral inducing agent, a chiral auxiliary reagent and zinc halide in an organic solvent in the presence of an alkaline reagent and a sulfonate or a sulphinate to obtain a first reaction mixture; (2) reacting the resultant first reaction mixture with 5-chloro-2-aminotrifluorobenzophenone to form (S)-2-amino-5-chloro-α-cyclopropyl acetylene-α-trifluoromethylbenzyl alcohol. The process avoids an organic zinc reagent and a Grignard reagent, and has the advantages of safe production, an environmentally friendly route, low production costs, a high resultant product yield, a high chiral ee value and is suitable for industrial production.

20 Claims, No Drawings

(56) References Cited

FOREIGN PATENT DOCUMENTS

| | | |
|---|---|---|
| CN | 103249725 A | 8/2013 |
| CN | 103833560 A | 6/2014 |
| WO | 98/51676 A1 | 11/1998 |
| WO | 2009/095931 A2 | 8/2009 |
| WO | 2010/059859 A1 | 5/2010 |
| WO | 2010/115638 A2 | 10/2010 |
| WO | 2010/115639 A1 | 10/2010 |

OTHER PUBLICATIONS

English Abstract of CN 1449865 A published Oct. 22, 2003.
English Abstract of CN 101125834 A published Feb. 20, 2008.
English Abstract of CN 101786959 A published Jul. 28, 2010.
English Abstract of CN 102617366 A published Aug. 1, 2012.
English Abstract of CN 103249724 A published Aug. 14, 2013.
English Abstract of CN 103249725 A published Aug. 14, 2013.
English Abstract of CN 103833560 A published Jun. 4, 2014.

\* cited by examiner

SYNTHESIS PROCESS FOR CHIRAL CYCLOPROPYL ETHYNYL TERTIARY ALCOHOL COMPOUND

FIELD OF THE INVENTION

The present invention relates to the field of organic synthetic chemistry and, in particular, to a method for the synthesis of (S)-2-amino-5-chloro-α-cyclopropyl acetylene-α-trifluoromethylbenzyl alcohol.

BACKGROUND

Efavirenz is a non-nucleoside reverse transcriptase inhibitor, developed by Merck, the chemical name of which is (S)-6-chloro-4-(cyclopropyl ethynyl)-1,4-dihydrogen-4-(trifluoromethyl)-2H-3,1-benzoxazine-2-ketone, the structure of which is shown as follows:

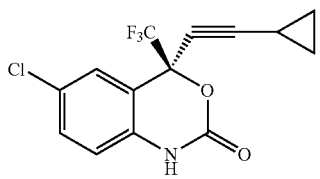 [SMILES: O=C1Nc2ccc(Cl)cc2[C@@](C#CC2CC2)(C(F)(F)F)O1]

Efaviren was approved by the FDA, US for anti-human immunodeficiency virus (HIV) infection in 1998 to inhibit HIV-1 reverse transcriptase, which is the preferred drug of non-nucleoside reverse transcriptase inhibitors (NNRTI) recommended by current international AIDS treatment guidelines.

(S)-2-amino-5-chloro-α-cyclopropyl acetylene-α-trifluoromethylbenzyl alcohol is a key intermediate for the synthesis of efavirenz. At present, there are four main methods reported for synthesizing the compound.

Method 1 is a synthetic route reported in WO9845278:

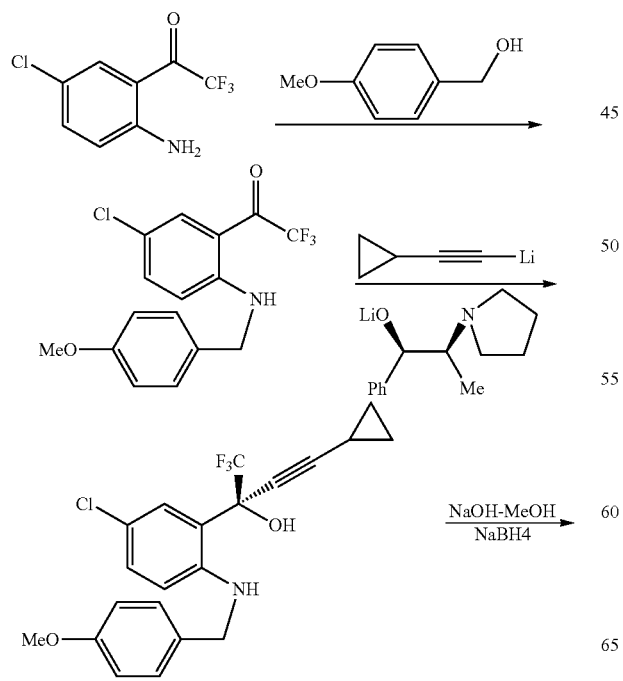

Method 2 is a synthetic method reported in WO9851676:

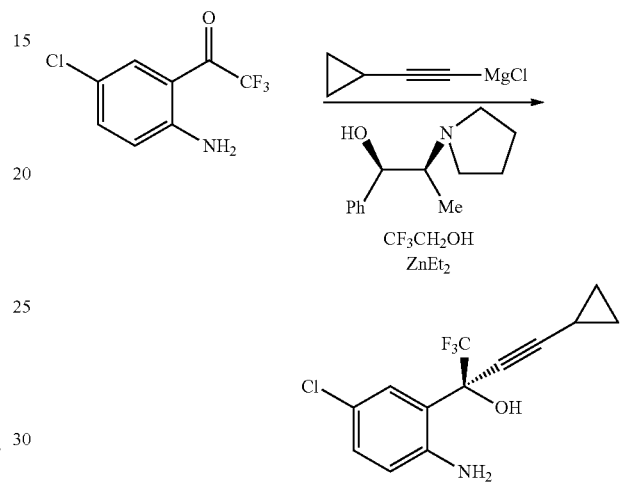

However, alkaline reagents are used in the asymmetric synthesis step of the above two methods. Butyl lithium is used in the method 1 and diethyl zinc is used in the method 2. The two reagents are not only expensive, but also belong to high-risk chemicals, which need strict storage conditions. The industrial use is not convenient and production accidents easily occur.

Method 3 is a synthetic method reported in CN1449865A:

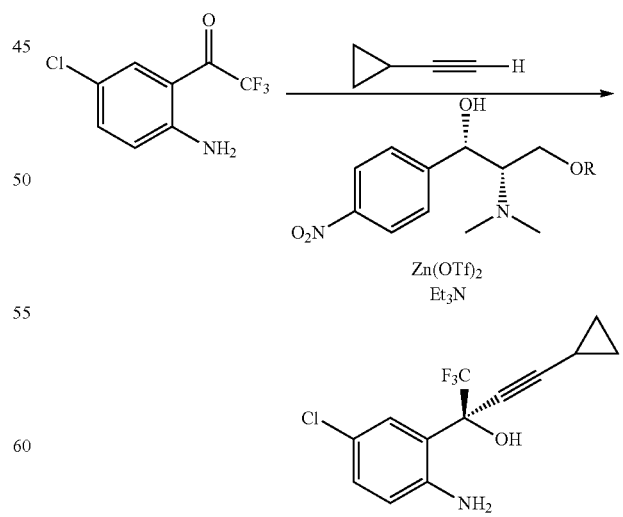

In method 3, diethyl zinc in the method 2 is replaced with zinc trifluoromethanesulfonate. Although the risk of production is avoided, the zinc trifluoromethanesulfonate is not easily available and the price is also expensive. Similarly, it is not suitable for industrial production.

Method 4 is a synthetic method reported in WO2009095931:

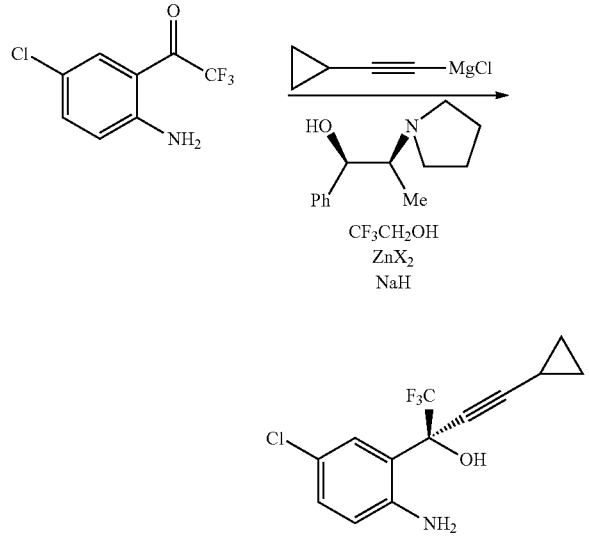

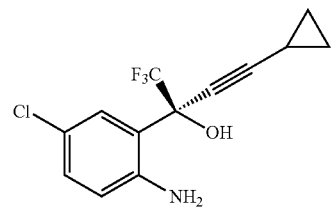 [SMILES: Nc1ccc(Cl)cc1[C@@](O)(C#CC1CC1)C(F)(F)F]

Alkaline reagents, such as sodium hydride and zinc halide, are used in method 4, instead of diethy lzinc, which can form complexes of zinc to participate in the subsequent addition reaction as well, whereas this method still requires the use of Grignard reagent of cyclopropyl magnesium chloride. As we all know, Grignard reagent is very sensitive to water. If the materials and equipment are not dry enough in the reaction process, it is likely to cause the reaction to fail, affecting product yield. Furthermore, Grignard reaction is violent, which has strict requirements to temperature and feeding velocity. Improper operation can easily lead to the reaction out of control, and even cause the consequences of a fire, thean explosion.

Therefore, there is an urgent need in the art for the improvement of synthesis and production methods to ensure the reaction route safe and under control, raw materials easy to be obtained and a high yield, suitable for industrial production.

SUMMARY OF THE INVENTION

The object of the present invention is to provide a novel synthetic method for (S)-2-amino-5-chloro-α-cyclopropyl acetylene-α-trifluoromethyl benzenemethanol.

In the first aspect of the present invention, a method for synthesizing a chiral cyclopropyl ethynyl tertiary alcohol compound is provided, said method comprises the following steps:

(1) In an organic solvent, in the presence of an alkaline reagent and a salt thereof, reacting cyclopropyl acetylene with a chiral inducing agent, a chiral auxiliary reagent and zinc halide, thereby obtaining a first reaction mixture;

(2) reacting the first reaction mixture obtained in step (1) with 5-chloro-2-aminotrifluorobenzophenone to form a compound of formula I:

that is (S)-2-amino-5-chloro-α-cyclopropyl acetylene-α-trifluoromethylbenzyl alcohol;

Wherein the salt is a sulfonate, a sulfinate, or a combination thereof.

In another preferred embodiment, said salt is a sulfonate.

In another preferred embodiment, the organic solvent is selected from the group consisting of: tetrahydrofuran, toluene, methyl tert-butyl ether, N-methylpyrrolidone, dioxane, diethyl ether, substituted or unsubstituted alkylbenzene, benzene, dichloromethane, cyclohexane, n-hexane, or combinations thereof.

In another preferred embodiment, the alkaline agent is selected from alkali hydrides, sodium alkoxides, potassium alkoxides, or combinations thereof; preferably NaH.

In another preferred embodiment, the sulfonate is selected from alkyl sulfonates, substituted or unsubstituted aryl sulfonates, or combinations thereof; and/or The sulfinate is selected from alkyl sulfinate, substituted or unsubstituted aryl sulfinate, or combinations thereof.

In another preferred embodiment, the alkyl sulfinate is selected from sodium methanesulfinate, magnesium methylsulfinate, zinc methylsulfinate, ammonium methylsulfinate, or combinations thereof, preferably sodium methylsulfinate.

In another preferred embodiment, the substituted arylsulfinate is selected from sodium p-tolylsulfinate, magnesium p-tolylsulfinate, zinc p-tolylsulfinate, ammonium p-tolylsulfinate, or combinations thereof, preferably sodium p-tolylsulfinate.

In another preferred embodiment, the salt is a mixture of sodium methanesulfonate and methanesulfinic acid sodium salt.

In another preferred embodiment, the chiral inducing agent is selected from chiral aminoalcohol or (S)-2-amino-5-chloro-α-cyclopropyl acetylene-α-trifluoromethylbenzyl alcohol.

In another preferred embodiment, the chiral aminoalcohol is selected from the group consisting of: (1R,2S)—N-pyrrolidyl norephedrine, (+)-N,N-dimethyl-α-(hydroxymethyl)-β-hydroxy-p-nitro-phenyl-ethylamine, N-methyl ephedrine, ephedrine, N,N-dibenzyl norephedrine, norephedrine, pseudoephedrine or (1S,2S)—N-methyl norephedrine, or a combination thereof.

In another preferred embodiment, the chiral auxiliary reagent is selected from alcohols; preferably, trifluoroethanol, trichloroethanol, t-butanol, neopentyl alcohol, triphenylcarbinol, isopropanol, ethanol, methanol, or a combination thereof.

In another preferred embodiment, the reaction temperature in the step (2) is 0-20° C., preferably 5-15° C.; and/or The reaction time is 2-6 hours, preferably 3-4 hours.

In another preferred embodiment, said method also comprises one or more of the following characteristics:

The molar ratio of the alkaline reagent to 5-chloro-2-aminotrifluorobenzophenone is 5-10:0.8-1.2;

The molar ratio of the sulfonate to 5-chloro-2-aminotrifluorobenzophenone is 0.5-1.5:0.8-1.2;

The molar ratio of the sulfinate to 5-chloro-2-aminotrifluorobenzophenone is 0.5-1.5:0.8-1.2.

The molar ratio of the zinc halide to the 5-chloro-2-aminotrifluorobenzophenone is 1.2-2.5:0.8-1.2;

The molar ratio of the cyclopropyl acetylene to 5-chloro-2-aminotrifluorobenzophenone is 1.1-2.0:0.8-1.2;

The molar ratio of the chiral inducing agent to 5-chloro-2-aminotrifluorobenzophenone is 1.2-1.5:0.8-1.2;

The molar ratio of the chiral auxiliary reagent to 5-chloro-2-aminotrifluorobenzophenone is 0.9-1.0:0.8-1.2;

The molar ratio of said alkaline reagent, sulfonate or sulfinate, zinc halide, cyclopropyl acetylene, chiral inducing agent, chiral auxiliary reagent and substrate 5-chloro-2-aminotrifluorobenzophenone is 5-10:0.5-1.5:1.2-2.5:1.1-2.0:1.2-1.5:0.9-1.0:0.8-1.2, preferably 6-9:0.8-1.3:1.5-2.5: 1.2-1.7:1.4-1.5:0.93-0.97:0.9-1.1.

In another preferred embodiment, after step (2), the method also comprises the following step: the compound of formula I is isolated and/or purified from the reaction mixture formed in step (2).

In another preferred embodiment, the method does not use the Grignard reagent.

It should be understood that, within the scope of the present invention, the technical features specifically described above and below (such as the Examples) can be combined with each other, thereby constituting a new or preferred technical solution which needs not be described one by one.

DETAILED DESCRIPTION OF THE INVENTION

Upon extensive and in-depth research, the inventors, for the first time, have found a novel method for the synthesis of (S)-2-amino-5-chloro-α-cyclopropyl acetylene-α-trifluoromethylbenzyl alcohol by extensive screening and testing. This method avoids the preparation and use of organic zinc reagent and Grignard reagent. It has the advantages of safe production, environment-friendly route, few production equipment and low production costs. Furthermore, the ee value of the product is >99%, which is very suitable for industrial production. Based on this, the present invention is accomplished.

Organic Zinc Complex

As used herein, the terms "organic zinc complex" and "organic zinc clathrate" are used interchangeably, referring to the reaction product present in the first reaction mixture formed by the reaction of zinc halide, chiral inducing agent, chiral auxiliary reagent, with cyclopropyl acetylene in the presence of an alkaline reagent and a sulfonate.

Alkaline Reagent

The alkaline agent of the present invention is selected from alkali hydrides, sodium alkoxides, potassium alkoxides, or combinations thereof; the preferred alkaline reagent is NaH.

Chiral Inducing Agent

The chiral inducing agent of the present invention is selected from chiral aminoalcohol or (S)-2-amino-5-chloro-α-cyclopropyl acetylene-α-trifluoromethylbenzyl alcohol which has an ee value of 99% or more.

The chiral aminoalcohol is preferably selected from (1R, 2S)—N-pyrrolidyl norephedrine, (+)-N,N-dimethyl-α-(hydroxymethyl)-β-hydroxy-p-nitro-phenyl-ethylamine, N-methyl ephedrine, ephedrine, N,N-dibenzyl norephedrine, norephedrine, pseudoephedrine or (1S,2S)—N-methyl norephedrine, or a combination thereof.

Chiral Auxiliary Reagent

The chiral auxiliary reagent of the present invention is selected from alcohols;

Preferably: trifluoroethanol, trichloroethanol, t-butanol, neopentyl alcohol, triphenylcarbinol, isopropanol, ethanol, methanol, or a combination thereof.

Synthetic Method

Provided is a synthesis process for a chiral cyclopropyl ethynyl tertiary alcohol compound, and the method comprises the following steps:

(1) In an organic solvent, in the presence of an alkaline reagent and a salt thereof, reacting cyclopropyl acetylene with a chiral inducing agent, a chiral auxiliary reagent and zinc halide, thereby obtaining a first reaction mixture;

(2) reacting the first reaction mixture obtained in step (1) with 5-chloro-2-aminotrifluorobenzophenone to form a compound of formula I:

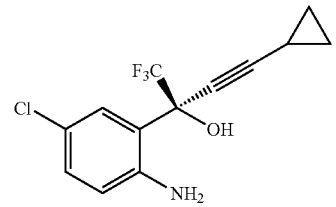 [SMILES: Nc1ccc(Cl)cc1[C@@](O)(C#CC1CC1)C(F)(F)F]

that is (S)-2-amino-5-chloro-α-cyclopropyl acetylene-α-trifluoromethylbenzyl alcohol;

Wherein the salt is a sulfonate, a sulfinate, or a combination thereof.

In another preferred embodiment, said salt is a sulfonate.

In another preferred embodiment, the organic solvent is selected from the group consisting of: tetrahydrofuran, toluene, methyl tert-butyl ether, N-methylpyrrolidone, dioxane, diethyl ether, substituted or unsubstituted alkylbenzene, benzene, dichloromethane, cyclohexane, n-hexane, or combinations thereof.

In another preferred embodiment, the alkaline agent is selected from alkali hydrides, sodium alkoxides, potassium alkoxides, or combinations thereof; preferably NaH.

In another preferred embodiment, the sulfonate is selected from alkyl sulfonates, substituted or unsubstituted aryl sulfonates, or combinations thereof; and/or The sulfinate is selected from alkyl sulfinate, substituted or unsubstituted aryl sulfinate, or combinations thereof.

In another preferred embodiment, the alkyl sulfinate is selected from sodium methanesulfinate, magnesium methylsulfinate, zinc methylsulfinate, ammonium methylsulfinate, or combinations thereof, preferably sodium methylsulfinate.

In another preferred embodiment, the substituted arylsulfinate is selected from sodium p-tolylsulfinate, magnesium p-tolylsulfinate, zinc p-tolylsulfinate, ammonium p-tolylsulfinate, or combinations thereof, preferably sodium p-tolylsulfinate.

In another preferred embodiment, the salt is a mixture of sodium methanesulfonate and methanesulfinic acid sodium salt.

In another preferred embodiment, the chiral inducing agent is selected from chiral aminoalcohol or (S)-2-amino-5-chloro-α-cyclopropyl acetylene-α-trifluoromethylbenzyl alcohol.

In another preferred embodiment, the chiral aminoalcohol is selected from the group consisting of: (1R,2S)—N-pyrrolidyl norephedrine, (+)-N,N-dimethyl-α-(hydroxymethyl)-β-hydroxy-p-nitro-phenyl-ethylamine, N-methyl ephedrine, ephedrine, N,N-dibenzyl norephedrine, norephedrine, pseudoephedrine or (1S,2S)—N-methyl norephedrine, or a combination thereof.

In another preferred embodiment, the chiral auxiliary reagent is selected from alcohols; preferably, trifluoroethanol, trichloroethanol, t-butanol, neopentyl alcohol, triphenylcarbinol, isopropanol, ethanol, methanol, or a combination thereof.

In another preferred embodiment, the reaction temperature in the step (2) is 0-20° C., preferably 5-15° C.; and/or The reaction time is 2-6 hours, preferably 3-4 hours.

In another preferred embodiment, said method also comprises one or more of the following characteristics:

The molar ratio of the alkaline reagent to 5-chloro-2-aminotrifluorobenzophenone is 5-10:0.8-1.2;

The molar ratio of the sulfonate to 5-chloro-2-aminotrifluorobenzophenone is 0.5-1.5:0.8-1.2;

The molar ratio of the sulfinate to 5-chloro-2-aminotrifluorobenzophenone is 0.5-1.5:0.8-1.2.

The molar ratio of the zinc halide to the 5-chloro-2-aminotrifluorobenzophenone is 1.2-2.5:0.8-1.2;

The molar ratio of the cyclopropyl acetylene to 5-chloro-2-aminotrifluorobenzophenone is 1.1-2.0:0.8-1.2;

The molar ratio of the chiral inducing agent to 5-chloro-2-aminotrifluorobenzophenone is 1.2-1.5:0.8-1.2;

The molar ratio of the chiral auxiliary reagent to 5-chloro-2-aminotrifluorobenzophenone is 0.9-1.0:0.8-1.2;

The molar ratio of said alkaline reagent, sulfonate or sulfinate, zinc halide, cyclopropyl acetylene, chiral inducing agent, chiral auxiliary reagent and substrate 5-chloro-2-aminotrifluorobenzophenone is 5-10:0.5-1.5:1.2-2.5:1.1-2.0:1.2-1.5:0.9-1.0:0.8-1.2, preferably 6-9:0.8-1.3:1.5-2.5:1.2-1.7:1.4-1.5:0.93-0.97:0.9-1.1.

In another preferred embodiment, after step (2), the method also comprises the following step: the compound of formula I is isolated and/or purified from the reaction mixture formed in step (2).

In another preferred embodiment, the method does not use the Grignard reagent.

The Main Advantages of the Invention Include:

Compared with the prior art, the synthetic method of the present invention avoids the preparation and use of organic zinc reagent and Grignard reagent. It has the advantages of safe production, environment-friendly route, few production equipment and low production costs. Furthermore, the ee value of the product is >99%, which is very suitable for industrial production.

The invention will be further illustrated with reference to the following specific examples. It should be understood that these examples are only intended to illustrate the invention, but not to limit the scope of the invention. The experimental methods in the following examples without particular conditions mentioned are performed under routine conditions or as instructed by the manufacturer. Unless indicated otherwise, parts and percentage are calculated by weight.

Example 1

800 ml of tetrahydrofuran, NaH (40.0 g, 1.67 mol) and sodium methanesulfonate (50.0 g, 0.42 mol) were added to a reaction flask. The mixture was cooled to −5-0° C. in an ice bath, and then zinc chloride (90.0 g, 0.66 mol) was added. Cyclopropyl acetylene (42.0 ml, 0.54 mol) was slowly added under heat preservation. After the addition, the mixture was stirred for 4 hours under heat preservation. A premixture of NaH (30.0 g, 1.25 mol), (1R,2S)—N-pyrrole norephedrine (133.0 g, 0.65 mol) and trifluoroethanol (31.0 ml, 0.43 mol) was added. After the system was naturally warmed to room temperature, keep the temperature for 1-2 hours. The reaction mixture was cooled to about 10° C., 5-chloro-2-aminotrifluorobenzophenone (100.0 g, 0.45 mol) was added and the reaction was carried out for 3 hours under heat preservation. After reaction is finished, the reaction was stopped by adding saturated ammonium chloride solution. Extracted with methyl tert-butyl ether, the organic layer was separated and then the organic layer was washed with 5% citric acid. The aqueous layer was extracted with methyl tert-butyl ether once, and the organic layer was combined and dried on anhydrous magnesium sulfate and concentrated under reduced pressure to give 123 g of (S)-2-amino-5-chloro-α-cyclopropyl acetylene-α-trifluoromethylbenzyl alcohol as the product, 95% yield, 99.8% HPLC purity, 99.5% ee value.

Example 2

400 ml of tetrahydrofuran, NaH (19.9 g, 0.83 mol) and sodium methanesulfonate (20.4 g, 0.2 mol) were added to a reaction flask. The mixture was cooled to −5-0° C. in an ice bath, and then zinc chloride (45.0 g, 0.33 mol) was added. Cyclopropyl acetylene (20.0 ml, 0.27 mol) was slowly added under heat preservation. After the addition, the mixture was stirred for 4 hours under heat preservation. A premixture of NaH (15.0 g, 0.62 mol), (1R,2S)—N-pyrrole norephedrine (65.5 g, 0.32 mol) and trifluoroethanol (15.9 ml, 0.22 mol) was added. After the system was naturally warmed to room temperature, keep the temperature for 1-2 hours. The reaction mixture was cooled to about 10° C., 5-chloro-2-aminotrifluorobenzophenone (50.0 g, 0.22 mol) was added and the reaction was carried out for 3 hours under heat preservation. After reaction was finished, the reaction was stopped by adding saturated ammonium chloride solution. Extracted with methyl tert-butyl ether, the organic layer was separated and then the organic layer was washed with 5% citric acid. The aqueous layer was extracted with methyl tert-butyl ether, and the organic layer was combined and dried on anhydrous magnesium sulfate and concentrated under reduced pressure to give 61.2 g of (S)-2-amino-5-chloro-α-cyclopropyl acetylene-α-trifluoromethylbenzyl alcohol as the product, 94.5% yield, 99.4% HPLC purity, 99.6% ee value.

Example 3

800 ml of tetrahydrofuran, NaH (40.0 g, 1.67 mol), sodium methanesulfonate (23.8 g, 0.2 mol) and methanesulfinic acid sodium salt (19.4 g, 0.22 mol) were added to a reaction flask. The mixture was cooled to −5-0° C. in an ice bath, and then zinc chloride (90.0 g, 0.66 mol) was added. Cyclopropy 1 acetylene (42.0 ml, 0.54 mol) was slowly added under heat preservation. After the addition, the mixture was stirred for 4 hours under heat preservation. A premixture of NaH (30.0 g, 1.25 mol), (1R,2S)—N-pyrrole norephedrine (133.0 g, 0.65 mol) and trifluoroethanol (31.0 ml, 0.43 mol) was added. After the system was naturally warmed to room temperature, keep the temperature for 1-2 hours. The reaction mixture was cooled to about 10° C., 5-chloro-2-aminotrifluorobenzophenone (100.0 g, 0.45 mol) was added and the reaction was carried out for 3 hours under heat preservation. After reaction was finished, the reaction was stopped by adding saturated ammonium chloride solution. Extracted with methyl tert-butyl ether, the organic layer was separated and then the organic layer was washed with 5% citric acid. The aqueous layer was extracted with methyl tert-butyl ether, and the organic layer was combined and dried on anhydrous magnesium sulfate and concentrated under reduced pressure to give 120.4 g of (S)-2-amino-5-chloro-α-cyclopropyl acetylene-α-trifluoromethylbenzyl alcohol as the product, 93.5% yield, 99.7% HPLC purity, 99.5% ee value.

Example 4

110 ml of toluene, sodium methylate (9.2 g, 0.17 mol) and magnesium methane sulfonate (7.0 g, 0.06 mol) were added to a reaction flask. The mixture was cooled to −5-0° C. in an ice bath, and then zinc chloride (9.0 g, 0.07 mol) was added. Cyclopropyl acetylene (5.7 ml, 0.074 mol) was slowly added under heat preservation. After the addition, the mixture was stirred for 5 hours under heat preservation. A premixture of sodium methylate (6.7 g, 0.13 mol), (1R, 2S)—N-pyrrole norephedrine (13.3 g, 0.065 mol) and trifluoroethanol (3.2 ml, 0.044 mol) was added. After the system was naturally warmed to room temperature, keep the temperature for 2-3 hours. The reaction mixture was cooled to about 15° C., 5-chloro-2-aminotrifluorobenzophenone (10.0 g, 0.045 mol) was added and the reaction was carried out for 3-4 hours under heat preservation. After reaction was finished, the reaction was stopped by adding saturated ammonium chloride solution. Extracted with methyl tert-butyl ether, the organic layer was separated and then the organic layer was washed with 5% citric acid. The aqueous layer was extracted with methyl tert-butyl ether, and the organic layer were combined and dried on anhydrous magnesium sulfate and concentrated under reduced pressure to give 10.0 g of (S)-2-amino-5-chloro-α-cyclopropyl acetylene-α-trifluoromethylbenzyl alcohol as the product, 77% yield, 99.6% HPLC purity, 99.3% ee value.

Example 5

800 ml of tetrahydrofuran, NaH (40.0 g, 1.67 mol) and magnesium methanesulfonate (37.4 g, 0.42 mol) were added to a reaction flask. The mixture was cooled to −5-0° C. in an ice bath, and then zinc chloride (90.0 g, 0.66 mol) was added. Cyclopropyl acetylene (42.0 ml, 0.54 mol) was slowly added under heat preservation. After the addition, the mixture was stirred for 4 hours under heat preservation. A premixture of NaH (30.0 g, 1.25 mol), (1R,2S)—N-pyrrole norephedrine (133.0 g, 0.65 mol) and trifluoroethanol (31.0 ml, 0.43 mol) was added. After the system was naturally warmed to room temperature, keep the temperature for 1-2 hours. The reaction mixture was cooled to about 10° C., 5-chloro-2-aminotrifluorobenzophenone (100.0 g, 0.45 mol) was added and the reaction was carried out for 3 hours under heat preservation. After reaction was finished, the reaction was stopped by adding saturated ammonium chloride solution. Extracted with methyl tert-butyl ether, the organic layer was separated and then the organic layer was washed with 5% citric acid. The aqueous layer was extracted with methyl tert-butyl ether, and the organic layer was combined and dried on anhydrous magnesium sulfate and concentrated under reduced pressure to give 89.3 g of (S)-2-amino-5-chloro-α-cyclopropyl acetylene-α-trifluoromethylbenzyl alcohol as the product, 69.5% yield, 99.6% HPLC purity, 99.3% ee value.

Example 6

120 ml of tetrahydrofuran, NaH (4.0 g, 0.17 mol) and magnesium methane sulfonate (7.0 g, 0.06 mol) were added to a reaction flask. The mixture was cooled to −5° C. in an ice bath, and then zinc bromide (15.7 g, 0.07 mol) was added. Cyclopropyl acetylene (5.7 ml, 0.074 mol) was slowly added under heat preservation. After the addition, the mixture was stirred for 3-4 hours under heat preservation. A premixture of NaH (3.0 g, 0.13 mol), (+)-N,N-dimethyl-α-(hydroxymethyl)-β-hydroxy-p-nitro-phenyl-ethylamine (13.7 g, 0.065 mol) and trifluoroethanol (3.1 ml, 0.043 mol) was added. After the system was naturally warmed to room temperature, keep the temperature for 1-2 hours. The reaction mixture was cooled to about 5° C., 5-chloro-2-aminotrifluorobenzophenone (10.0 g, 0.045 mol) was added and the reaction was carried out for 3 hours under heat preservation. After reaction was finished, the reaction was stopped by adding saturated ammonium chloride solution. Extracted with methyl tert-butyl ether, the organic layer was separated and then the organic layer was washed with 5% citric acid. The aqueous layer was extracted with methyl tert-butyl ether, and the organic layer was combined and dried on anhydrous magnesium sulfate and concentrated under reduced pressure to give 11.0 g of (S)-2-amino-5-chloro-α-cyclopropyl acetylene-α-trifluoromethylbenzyl alcohol as the product, 85% yield, 97.3% HPLC purity, 99.1% ee value.

Example 7

100 ml of toluene, NaH (6.0 g, 0.25 mol) and methanesulfinic acid sodium salt (6.1 g, 0.06 mol) were added to a reaction flask. The mixture was cooled to −5° C. in an ice bath, and then zinc bromide (15.7 g, 0.07 mol) was added. Cyclopropyl acetylene (4.2 ml, 0.054 mol) was slowly added under heat preservation. After the addition, the mixture was stirred for 3-4 hours under heat preservation. A premixture of sodium methylate (4.0 g, 0.017 mol), (1R, 2S)—N-pyrrole norephedrine (13.3 g, 0.065 mol) and trifluoroethanol (3.1 ml, 0.043 mol) was added. After the system was naturally warmed to room temperature, keep the temperature for 1-2 hours. The reaction mixture was cooled to about 5° C., 5-chloro-2-aminotrifluorobenzophenone (10.0 g, 0.045 mol) was added and the reaction was carried out for 3 hours under heat preservation. After reaction was finished, the reaction was stopped by adding saturated ammonium chloride solution. Extracted with methyl tert-butyl ether, the organic layer was separated and then the organic layer was washed with 5% citric acid. The aqueous layer was extracted with methyl tert-butyl ether, and the organic layer was combined and dried on anhydrous magnesium sulfate and concentrated under reduced pressure to give 10.2 g of (S)-2-amino-5-chloro-α-cyclopropyl acetylene-α-trifluoromethylbenzyl alcohol as the product, 79% yield, 97.6% HPLC purity, 99.3% ee value.

Example 8

100 ml of tetrahydrofuran, NaH (6.0 g, 0.25 mol) and zinc methanesulfonate (15.3 g, 0.04 mol) were added to a reaction flask. The mixture was cooled to 0° C. in an ice bath, and then zinc chloride (15.0 g, 0.11 mol) was added. Cyclopropy 1 acetylene (4.2 ml, 0.054 mol) was slowly added under heat preservation. After the addition, the mixture was stirred for 4 hours under heat preservation. A premixture of NaH (3.0 g, 0.13 mol), N,N-dibenzyl norephedrine (9.8 g, 0.065 mol) and trichloroethanol (4.1 ml, 0.043 mol) was added. After the system was naturally warmed to room temperature, keep the temperature for 2-3 hours. The reaction mixture was cooled to about 10° C., 5-chloro-2-aminotrifluorobenzophenone (10.0 g, 0.045 mol) was added and the reaction was carried out for 3 hours under heat preservation. After reaction was finished, the reaction was stopped by adding saturated ammonium chloride solution. Extracted with methyl tert-butyl ether, the organic layer was separated and then the organic layer was washed with 5% citric acid. The aqueous layer was extracted with methyl tert-butyl ether, and the organic layer was combined and dried on anhydrous magnesium sulfate and concentrated under reduced pressure to give 9.7 g of (S)-2-amino-5-chloro-α-cyclopropyl acetylene-α-trifluoromethylbenzyl alcohol as the product, 75% yield, 96.2% HPLC purity, 99.2% ee value.

Example 9

100 ml of tetrahydrofuran, sodium ethoxide (11.6 g, 0.17 mol) and magnesium methane sulfonate (5.0 g, 0.04 mol) were added to a reaction flask. The mixture was cooled to 0° C. in an ice bath, and then zinc chloride (9.0 g, 0.07 mol) was added. Cyclopropyl acetylene (4.2 ml, 0.054 mol) was slowly added under heat preservation. After the addition, the mixture was stirred for 4 hours under heat preservation. A premixture of sodium ethoxide (8.5 g, 0.13 mol), (1R,2S)—N-pyrrolidyl norephedrine (13.3 g, 0.065 mol) and trichloroethanol (4.1 ml, 0.043 mol) was added. After the system was naturally warmed to room temperature, keep the temperature for 3-4 hours. The reaction mixture was cooled to about 10° C., 5-chloro-2-aminotrifluorobenzophenone (10.0 g, 0.045 mol) was added and the reaction was carried out for 3-4 hours under heat preservation. After reaction was finished, the reaction was stopped by adding saturated ammonium chloride solution. Extracted with methyl tert-butyl ether, the organic layer separated and then the organic layer was washed with 5% citric acid. The aqueous layer was extracted with methyl tert-butyl ether, and the organic layer was combined and dried on anhydrous magnesium sulfate and concentrated under reduced pressure to give 10.0 g of (S)-2-amino-5-chloro-α-cyclopropyl acetylene-α-trifluoromethylbenzyl alcohol as the product, 77% yield, 97.8% HPLC purity, 99.3% ee value.

Example 10

150 ml of toluene, NaH (4.0 g, 0.17 mol) and methanesulfinic acid sodium salt (4.1 g, 0.04 mol) were added to a reaction flask. The mixture was cooled to 0° C. in an ice bath, and then zinc chloride (9.0 g, 0.07 mol) was added. Cyclopropyl acetylene (5.7 ml, 0.074 mol) was slowly added under heat preservation. After the addition, the mixture was stirred for 4 hours under heat preservation. A premixture of NaH (3.0 g, 0.13 mol), (1R,2S)—N-pyrrole norephedrine (13.3 g, 0.065 mol) and trifluoroethanol (3.1 ml, 0.043 mol) was added. After the system was naturally warmed to room temperature, keep the temperature for 1-2 hours. The reaction mixture was cooled to about 10° C., 5-chloro-2-aminotrifluorobenzophenone (10.0 g, 0.045 mol) was added and the reaction was carried out for 3-4 hours under heat preservation. After reaction was finished, the reaction was stopped by adding saturated ammonium chloride solution. Extracted with methyl tert-butyl ether, the organic layer was separated and then the organic layer was washed with 5% citric acid. The aqueous layer was extracted with methyl tert-butyl ether, and the organic layer was combined and dried on anhydrous magnesium sulfate and concentrated under reduced pressure give 11.9 g of (S)-2-amino-5-chloro-α-cyclopropyl acetylene-α-trifluoromethylbenzyl alcohol as the product, 92% yield, 99.6% HPLC purity, 99.5% ee value.

Example 11

100 ml of toluene, NaH (6.0 g, 0.25 mol) and methanesulfinic acid sodium salt (6.1 g, 0.06 mol) were added to a reaction flask. The mixture was cooled to −5° C. in an ice bath, and then zinc bromide (15.7 g, 0.07 mol) was added. Cyclopropyl acetylene (4.2 ml, 0.054 mol) was slowly added under heat preservation. After the addition, the mixture was stirred for 3-4 hours under heat preservation. A premixture of NaH (4.0 g, 0.17 mol), (S)-2-amino-5-chloro-α-cyclopropyl acetylene-α-trifluoromethylbenzyl alcohol (13.0 g, 0.045 mol) and trifluoroethanol (3.1 ml, 0.043 mol) was added. After the system was naturally warmed to room temperature, keep the temperature for 1-2 hours. The reaction mixture was cooled to about 5° C., 5-chloro-2-aminotrifluorobenzophenone (10.0 g, 0.045 mol) was added and the reaction was carried out for 3 hours under heat preservation. After reaction was finished, the reaction was stopped by adding saturated ammonium chloride solution. Extracted with methyl tert-butyl ether, the organic layer was separated and then the organic layer was washed with 5% citric acid. The aqueous layer was extracted with methyl tert-butyl ether, and the organic layer was combined and dried on anhydrous magnesium sulfate and concentrated under reduced pressure to give 8.0 g of (S)-2-amino-5-chloro-α-cyclopropyl acetylene-α-trifluoromethylbenzyl alcohol as the product, 62% yield, 97.6% HPLC purity, 96.0% ee value.

The product obtained was formed into a hydrochloride and then was separated with a aqueous solution of 5-30% sodium hydroxide. A product with high optical purity of ee value>99.0% was obtained.

Example 12

800 ml of tetrahydrofuran, NaH (30.0 g, 1.25 mol), sodium methanesulfonate (48.0 g, 0.4 mol), zinc chloride (70.0 g, 0.5 mol) and (1R,2S)—N-pyrrole norephedrine (133.0 g, 0.65 mol) were added to a reaction flask. The mixture was stirred for 1 hour at room temperature. After the mixture was cooled to about 20° C., trifluoroethanol (18.6 ml, 0.267 mol) was dropwise added and the mixture was stirred for 1 hour at room temperature. NaH (8.6 g, 0.215 mol) was added and the mixture was stirred for 20 minutes. Then the mixture was cooled to −5-0° C. in an ice-salt bath, and cyclopropyl acetylene (42 ml, 0.54 mol) was slowly dropwise added under heat preservation. After the addition, the mixture was stirred for 1-2 hours under heat preservation and the system was naturally warmed to 10-15° C., 5-chloro-2-aminotrifluorobenzophenone (100.0 g, 0.45 mol) was added and the reaction was carried out for 3 hours under heat preservation. After reaction was finished, the organic layer was washed with 5% citric acid and the organic layer was combined and concentrated. After concentrated, the system was dissolved by adding 500 ml isopropyl acetate. 50 g of HCl gas was bubbled into the system and the mixture was stirred for 1 hour to form salt. Then the mixture was filtered, and the filter cake was fully washed with 50 ml of isopropyl acetate and dried to give 122 g of (S)-2-amino-5-chloro-α- cyclopropyl acetylene-α-trifluoromethylbenzyl alcohol as the pure product, 94.3% yield, 99.8% HPLC purity, 99.7% ee value.

Example 13

The hydrochloride obtained in example 11 was used directly in the next step of cyclization reaction, instead of using the aqueous solution of sodium hydroxid to separate the product, and the final product of efavirenz was obtained. The reaction equation is shown as follows:

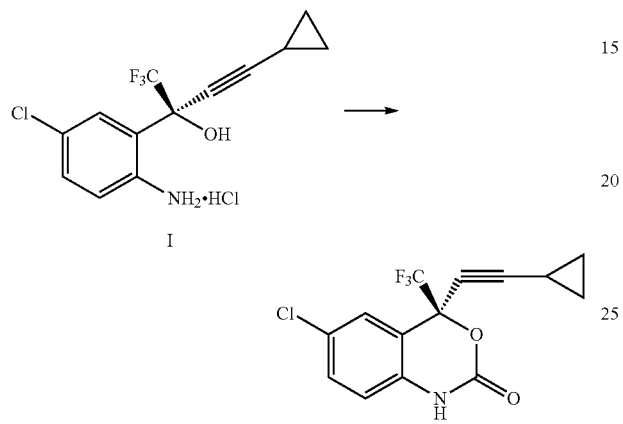

At room temperature, 6.0 g of (S)-2-amino-5-chloro-α-cyclopropyl acetylene-α-trifluoromethylbenzyl alcohol hydrochloride, 20 ml of toluene, 35 ml of water and 10.0 g of potassium bicarbonate were added to a reaction flask. The solid was dissolved by stirring. A solution of toluene (10 ml) containing 2.5 g of triphosgene was dropwise added. After the addition, the mixture was stirred for 2 hours at room temperature. After reaction was finished, the aqueous phase was removed and the organic phase was concentrated under reduced pressure until white solid comes out. Then 50 ml of n-heptane was added to give crystals and 9.0 g of efloxacin was obtained, 99.5% ee value.

NMR data of efaviren: $^1$H NMR ((CD$_3$)$_2$SO): δ 11.09 (s, 1H, N—H), 7.55 (m, 1H, C—H), 7.46 (d, 1H, C—H), 7.01 (d, 1H, C—H), 1.58 (m, 1H, C—H), 0.93 (m, 2H, C—H$_2$), 0.82 (m, 2H, C—H$_2$).

Contrast Example

In this example, example 7 was substantially repeated with the exception that no sulfonate was added.

As a result, the yield of (S)-2-amino-5-chloro-α-cyclopropyl acetylene-α-trifluoromethylbenzyl alcohol was less than 50%, the HPLC purity of the product was less than 85% and the ee value was less than 70%.

The contrast example shows that, in the absence of sulfonate or sulfinate, not only the yield of the product of (S)-2-amino-5-chloro-α-cyclopropyl acetylene-α-trifluoromethylbenzyl alcohol was decreased, but also the ee value was significantly decreased.

All literatures mentioned in the present application are incorporated herein by reference, as though each one is individually incorporated by reference. Additionally, it should be understood that after reading the above teachings, those skilled in the art can make various changes and modifications to the present invention. These equivalents also fall within the scope defined by the appended claims.

The invention claimed is:

1. A method for synthesizing a chiral cyclopropyl ethynyl tertiary alcohol compound, wherein the method comprises the following steps:
   (1) in an organic solvent, in the presence of an alkaline reagent and a salt thereof, reacting cyclopropyl acetylene with a chiral inducing agent, a chiral auxiliary reagent and zinc halide, thereby obtaining a first reaction mixture;
   (2) reacting the first reaction mixture obtained in step (1) with 5-chloro-2-aminotrifluorobenzophenone to form a compound of formula I:

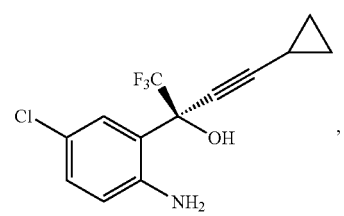

that is (S)-2-amino-5-chloro-α-cyclopropyl acetylene-α-trifluoromethylbenzyl alcohol;
wherein the salt is a sulfonate, a sulfinate, or a combination thereof;
and the alkaline agent is an alkali hydride.

2. The method according to claim 1, wherein said salt is a sulfonate.

3. The method according to claim 2, wherein the organic solvent is selected from the group consisting of: tetrahydrofuran, toluene, methyl tert-butyl ether, N-methylpyrrolidone, dioxane, diethyl ether, substituted alkylbenzene, unsubstituted alkylbenzene, benzene, dichloromethane, cyclohexane, and n-hexane, or is a combination thereof.

4. The method according to claim 2, wherein the alkaline agent is NaH.

5. The method according to claim 1, wherein the organic solvent is selected from the group consisting of: tetrahydrofuran, toluene, methyl tert-butyl ether, N-methylpyrrolidone, dioxane, diethyl ether, substituted alkylbenzene, unsubstituted alkylbenzene, benzene, dichloromethane, cyclohexane, and n-hexane, or is a combination thereof.

6. The method according to claim 1, wherein the sulfonate is selected from the group consisting of: alkyl sulfonates, substituted aryl sulfonates and unsubstituted aryl sulfonates, or is a combination thereof; and/or
   the sulfinate is selected from the group consisting of: alkyl sulfinate, substituted aryl sulfonate and unsubstituted aryl sulfinate, or is a combination thereof.

7. The method according to claim 1, wherein the chiral inducing agent is selected from the group consisting of: chiral aminoalcohol and (S)-2-amino-5-chloro-α-cyclopropyl acetylene-α-trifluoromethylbenzyl alcohol.

8. The method according to claim 1, wherein the chiral auxiliary reagent is an alcohol.

9. The method according to claim 8, wherein the chiral auxiliary reagent is selected from the group consisting of: trifluoroethanol, trichloroethanol, t-butanol, neopentyl alcohol, triphenylcarbinol, isopropanol, ethanol, and methanol, or is a combination thereof.

10. The method according to claim 1, wherein the reaction temperature in the step (2) is 0-20° C.; and/or the reaction time is 2-6 hours.

11. The method according to claim 10, wherein the reaction temperature in the step (2) is 5-15° C.

12. The method according to claim 10, wherein the reaction time is 3-4 hours.

13. The method according to claim 1, wherein said method also comprises one or more of the following characteristics:
the molar ratio of the alkaline reagent to 5-chloro-2-aminotrifluorobenzophenone is 5-10:0.8-1.2;
the molar ratio of the sulfonate to 5-chloro-2-aminotrifluorobenzophenone is 0.5-1.5:0.8-1.2;
the molar ratio of the sulfinate to 5-chloro-2-aminotrifluorobenzophenone is 0.5-1.5:0.8-1.2;
the molar ratio of the zinc halide to the 5-chloro-2-aminotrifluorobenzophenone is 1.2-2.5:0.8-1.2;
the molar ratio of the cyclopropyl acetylene to 5-chloro-2-aminotrifluorobenzophenone is 1.1-2.0:0.8-1.2;
the molar ratio of the chiral inducing agent to 5-chloro-2-aminotrifluorobenzophenone is 1.2-1.5:0.8-1.2;
the molar ratio of the chiral auxiliary reagent to 5-chloro-2-aminotrifluorobenzophenone is 0.9-1.0:0.8-1.2;
the molar ratio of said alkaline reagent, sulfonate or sulfinate, zinc halide, cyclopropyl acetylene, chiral inducing agent, chiral auxiliary reagent and substrate 5-chloro-2-aminotrifluorobenzophenone is 5-10:0.5-1.5:1.2-2.5:1.1-2.0:1.2-1.5:0.9-1.0:0.8-1.2.

14. The method according to claim 13, wherein the molar ratio of said alkaline reagent, sulfonate or sulfinate, zinc halide, cyclopropyl acetylene, chiral inducing agent, chiral auxiliary reagent and substrate 5-chloro-2-aminotrifluorobenzophenone is 6-9:0.8-1.3:1.5-2.5:1.2-1.7:1.4-1.5:0.93-0.97:0.9-1.1.

15. The method according to claim 1, wherein after step (2), the method also comprises the following step: the compound of formula I is isolated and/or purified from the reaction mixture formed in step (2).

16. The method according to claim 1, wherein a Grignard reagent is not used in the method.

17. The method according to claim 1, wherein the alkaline agent is NaH.

18. The method according to claim 1, wherein the sulfonate is selected from the group consisting of: alkyl sulfonates, substituted aryl sulfonatesm and unsubstituted aryl sulfonates, or is a combination thereof; and/or
the sulfinate is selected from the group consisting of: alkyl sulfinate, substituted aryl sulfonate and unsubstituted aryl sulfinate, or is a combination thereof.

19. The method according to claim 1, wherein the chiral inducing agent is selected from the group consisting of: chiral aminoalcohol and (S)-2-amino-5-chloro-α-cyclopropyl acetylene-α-trifluoromethylbenzyl alcohol.

20. The method according to claim 1, wherein the ee value of the (S)-2-amino-5-chloro-α-cyclopropyl acetylene-α-trifluoromethylbenzyl alcohol is >99%.

* * * * *